(12) United States Patent
Sakai et al.

(10) Patent No.: US 11,986,153 B2
(45) Date of Patent: May 21, 2024

(54) INSERTION ASSIST DEVICE FOR ENDOSCOPE AND ENDOSCOPE SYSTEM

(71) Applicant: OLYMPUS CORPORATION, Tokyo (JP)

(72) Inventors: Yuji Sakai, Kodaira (JP); Tetsuhide Takeyama, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 625 days.

(21) Appl. No.: 17/024,777

(22) Filed: Sep. 18, 2020

(65) Prior Publication Data

US 2021/0000333 A1 Jan. 7, 2021

Related U.S. Application Data (63) Continuation of application No. PCT/JP2018/039492, filed on Oct. 24, 2018.

(30) Foreign Application Priority Data

Mar. 19, 2018 (JP) .................. 2018-051242

(51) Int. Cl.
*A61B 1/00* (2006.01)
*A61B 1/01* (2006.01)
(Continued)

(52) U.S. Cl.
CPC ...... *A61B 1/00154* (2013.01); *A61B 1/00066* (2013.01); *A61B 1/00087* (2013.01);
(Continued)

(58) Field of Classification Search
CPC ............ A61B 1/00066; A61B 1/00112; A61B 1/00119; A61B 1/00121; A61B 1/00128;
(Continued)

(56) References Cited

U.S. PATENT DOCUMENTS 5,020,514 A * 6/1991 Heckele ............. A61B 1/00135
600/107
8,002,698 B2 * 8/2011 Motai .................. A61B 1/2736
600/116
(Continued)

FOREIGN PATENT DOCUMENTS

| JP | 2008-264517 A | 11/2008 |
| WO | 2016/117432 A1 | 7/2016 |
| WO | 2017/138533 A1 | 8/2017 |

OTHER PUBLICATIONS

English translation of International Preliminary Report on Patentability dated Oct. 1, 2020 together with the Written Opinion issued in International Application No. PCT/JP2018/039492.
(Continued)

*Primary Examiner* — Ryan N Henderson
(74) *Attorney, Agent, or Firm* — Scully, Scott, Murphy & Presser, P.C.

(57) ABSTRACT

An insertion assist device for an endoscope includes a grip, an operation portion, a liquid storage, and a tubular member. The grip includes a channel through an inside of which an insertion portion of the endoscope is inserted. The operation portion is configured to advance the insertion section by moving forward relative to the grip. The liquid storage is provided on an interior portion of the grip and configured to store a liquid. The tubular member is provided on an interior portion or an exterior portion of the insertion portion of the endoscope, is connected to the liquid storage at one end of the tubular member, and is configured to guide the liquid toward another end of the tubular member opposite to said one end.

19 Claims, 10 Drawing Sheets

(51) Int. Cl.
　　　*A61B 1/015*　　　(2006.01)
　　　*A61B 1/233*　　　(2006.01)
　　　*A61M 31/00*　　　(2006.01)
　　　*A61M 39/22*　　　(2006.01)

(52) U.S. Cl.
　　　CPC ...... *A61B 1/00121* (2013.01); *A61B 1/00128* (2013.01); *A61B 1/00131* (2013.01); *A61B 1/00135* (2013.01); *A61B 1/0014* (2013.01); *A61B 1/00147* (2013.01); *A61B 1/015* (2013.01); *A61B 1/233* (2013.01); *A61M 31/00* (2013.01); *A61M 39/22* (2013.01); *A61B 1/01* (2013.01); *A61M 2210/0681* (2013.01)

(58) Field of Classification Search
　　　CPC .............. A61B 1/00135; A61B 1/0014; A61B 1/00142; A61B 1/00154; A61B 1/233; A61B 1/015
　　　See application file for complete search history.

(56) References Cited

U.S. PATENT DOCUMENTS

| | | | | |
|---|---|---|---|---|
| 8,241,266 B2* | 8/2012 | Keith | | A61M 25/10 604/506 |
| 8,328,837 B2* | 12/2012 | Binmoeller | | A61M 25/104 604/164.01 |
| 9,278,199 B2* | 3/2016 | Keith | | A61M 25/0084 |
| 9,694,167 B2* | 7/2017 | Keith | | A61B 1/126 |
| 2001/0044570 A1* | 11/2001 | Ouchi | | A61B 1/018 600/107 |
| 2006/0063973 A1* | 3/2006 | Makower | | A61B 17/282 600/114 |
| 2006/0095066 A1* | 5/2006 | Chang | | A61B 17/12136 606/199 |
| 2008/0214890 A1* | 9/2008 | Motai | | A61B 1/018 600/107 |
| 2008/0228034 A1* | 9/2008 | Fujikura | | A61B 1/00082 600/114 |
| 2008/0249356 A1* | 10/2008 | Motai | | A61B 1/00082 600/114 |
| 2008/0275483 A1* | 11/2008 | Makower | | A61B 17/32053 600/114 |
| 2008/0287961 A1* | 11/2008 | Miyamoto | | A61B 1/018 606/127 |
| 2009/0030380 A1* | 1/2009 | Binmoeller | | A61B 1/018 604/509 |
| 2009/0054727 A1* | 2/2009 | Yamaya | | G02B 23/2469 600/107 |
| 2010/0069712 A1* | 3/2010 | Yamaya | | A61B 1/0125 600/113 |
| 2010/0099946 A1* | 4/2010 | Jenkins | | A61B 1/0014 606/199 |
| 2011/0301415 A1* | 12/2011 | Motai | | A61B 1/00082 600/114 |
| 2012/0071856 A1* | 3/2012 | Goldfarb | | A61M 25/0113 604/514 |
| 2012/0078041 A1* | 3/2012 | Kitano | | A61B 1/00098 600/107 |
| 2012/0283625 A1* | 11/2012 | Keith | | A61M 25/10 604/506 |
| 2013/0172673 A1* | 7/2013 | Kennedy, II | | A61B 1/2736 600/109 |
| 2013/0261388 A1* | 10/2013 | Jenkins | | A61B 17/24 600/104 |
| 2015/0073211 A1* | 3/2015 | Dickhans | | F16B 2/18 248/229.11 |
| 2015/0105818 A1* | 4/2015 | Keith | | A61M 29/02 606/196 |
| 2016/0045100 A1* | 2/2016 | Eto | | A61B 1/00087 600/106 |
| 2016/0073861 A1* | 3/2016 | Kaneko | | G02B 23/2476 600/125 |
| 2016/0198934 A1* | 7/2016 | Kapfermann | | A61B 1/0014 600/105 |
| 2016/0249796 A1* | 9/2016 | Fujisaki | | A61M 1/84 600/114 |
| 2016/0287059 A1* | 10/2016 | Ha | | A61M 29/02 |
| 2016/0287065 A1* | 10/2016 | Ha | | A61B 1/00154 |
| 2017/0172389 A1* | 6/2017 | Fujisaki | | A61B 1/00142 |
| 2017/0231481 A1* | 8/2017 | Kojo | | A61B 1/00172 600/114 |
| 2017/0311790 A1 | 11/2017 | Yoshida | | |
| 2018/0125515 A1* | 5/2018 | Jenkins | | A61M 25/0068 |

OTHER PUBLICATIONS

International Search Report dated Jan. 29, 2019 received in International Application No. PCT/JP2018/039492, together with an English-language translation.

* cited by examiner

INSERTION ASSIST DEVICE FOR ENDOSCOPE AND ENDOSCOPE SYSTEM

CROSS-REFERENCE TO RELATED APPLICATIONS

This application is a Continuation Application of PCT Application No. PCT/JP2018/039492, filed Oct. 24, 2018 and based upon and claiming the benefit of priority from prior Japanese Patent Application No. 2018-051242, filed Mar. 19, 2018, the entire contents of all of which are incorporated herein by reference.

FIELD

The present invention relates to an insertion assist device for an endoscope and an endoscope system for inserting an endoscope into a sinus of an examinee.

BACKGROUND

An endoscope including a handle with an operation lever is disclosed in, for example, Jpn. Pat. Appln. KOKAI Publication No. 2008-264517.

BRIEF SUMMARY OF THE INVENTION

According to one aspect of the present invention, an insertion assist device for an endoscope includes a grip, an operation portion, a liquid storage, and a tubular member. The grip includes a channel through an inside of which an insertion portion of the endoscope is inserted. The operation portion is configured to advance the insertion section by moving forward relative to the grip, and is configured to retreat the insertion section by moving backward relative to the grip. The liquid storage is provided on an interior portion of the grip and configured to store a liquid. The tubular member is provided on an interior portion or an exterior portion of the insertion portion of the endoscope, is connected to the liquid storage at one end of the tubular member, and is configured to guide the liquid toward another end of the tubular member opposite to said one end.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

First Embodiment

An embodiment of an endoscope system 11 will be described below with reference to FIGS. 1 to 14.

Figure 1:
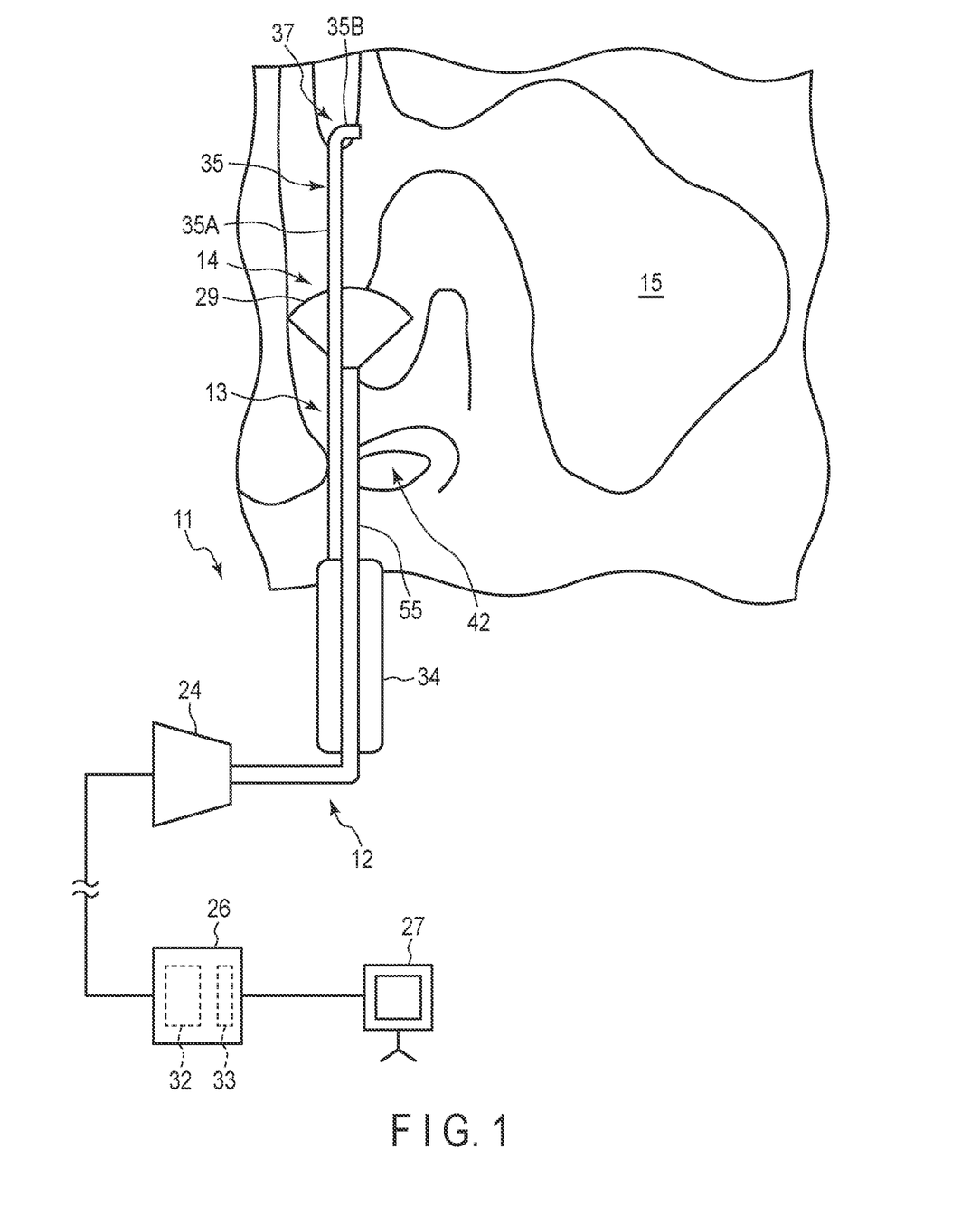
FIG. 1 is a schematic view showing an overall configuration of an endoscope system according to an embodiment.

As shown in FIG. 1, the endoscope system 11 includes an endoscope 12 and an insertion assist device 13 for an endoscope configured to guide the endoscope 12 into a sinus of the examinee. The endoscope 12 is configured of a so-called soft endoscope which has flexibility. The endoscope 12 may be configured of a scanning-type endoscope. The insertion assist device 13 is attached to the endoscope 12.

Figure 2:
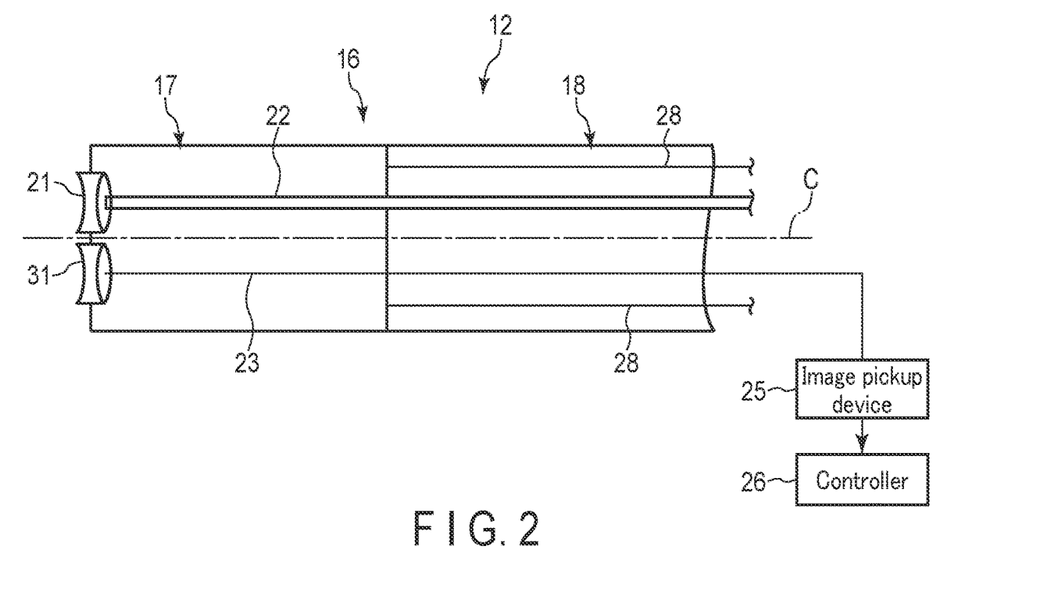
FIG. 2 is a schematic view schematically showing the vicinity of a distal component of an endoscope shown in FIG. 1.

As shown in FIGS. 1 and 2, the endoscope 12 includes: an insertion portion 16 used for insertion into a nasal cavity 14, the paranasal sinuses (a maxillary sinus 15), etc.; a distal component 17 provided on the vicinity of a distal end of the insertion portion 16; a bending portion 18 provided on the proximal side with respect to the distal component 17 and configured to adjust a direction in which the distal component 17 extends; a channel through which a treatment tool that performs a predetermined treatment on the interior of the sinus is passed; an illumination lens 21; a plurality of illumination fibers 22; a plurality of light-receiving fibers 23; a handle 24 for applying various operations (e.g., a bending operation) to the insertion portion 16; a controller 26 electrically connected to the insertion portion 16 and the image pickup device 25 by a power line and various signal lines; and a display 27 connected to the controller 26. A central axis C is defined along a longitudinal direction of the endoscope 12. The channel is provided on an interior portion of the insertion portion 16 over the entire length of the insertion portion 16, and a treatment tool can be passed through an interior portion of the channel.

The display 27 is configured of a general liquid crystal monitor, and can display an image acquired by the endoscope 12 as an image.

The bending portion 18 includes a rotatable joint portion and paired wires 28, 28 extending between the distal component 17 and the handle 24. The handle 24 includes, for example, a dial, and the paired wires 28, 28 are wound around a rotation shaft of the dial with a pulley or the like interposed therebetween. The user can pull the paired wires 28, 28 by rotating the dial. That is, when one of the pair of wires 28, 28 is pulled in accordance with the rotation of the dial and the other of the paired wires 28, 28 is loosened, the distal component 17 is pulled and the bending portion 18 is bent toward either the left or the right. In this manner, the user can make the bending portion 18 bend by operating the dial, thereby changing the direction in which the distal component 17 extends to a desired direction.

Figure 11:
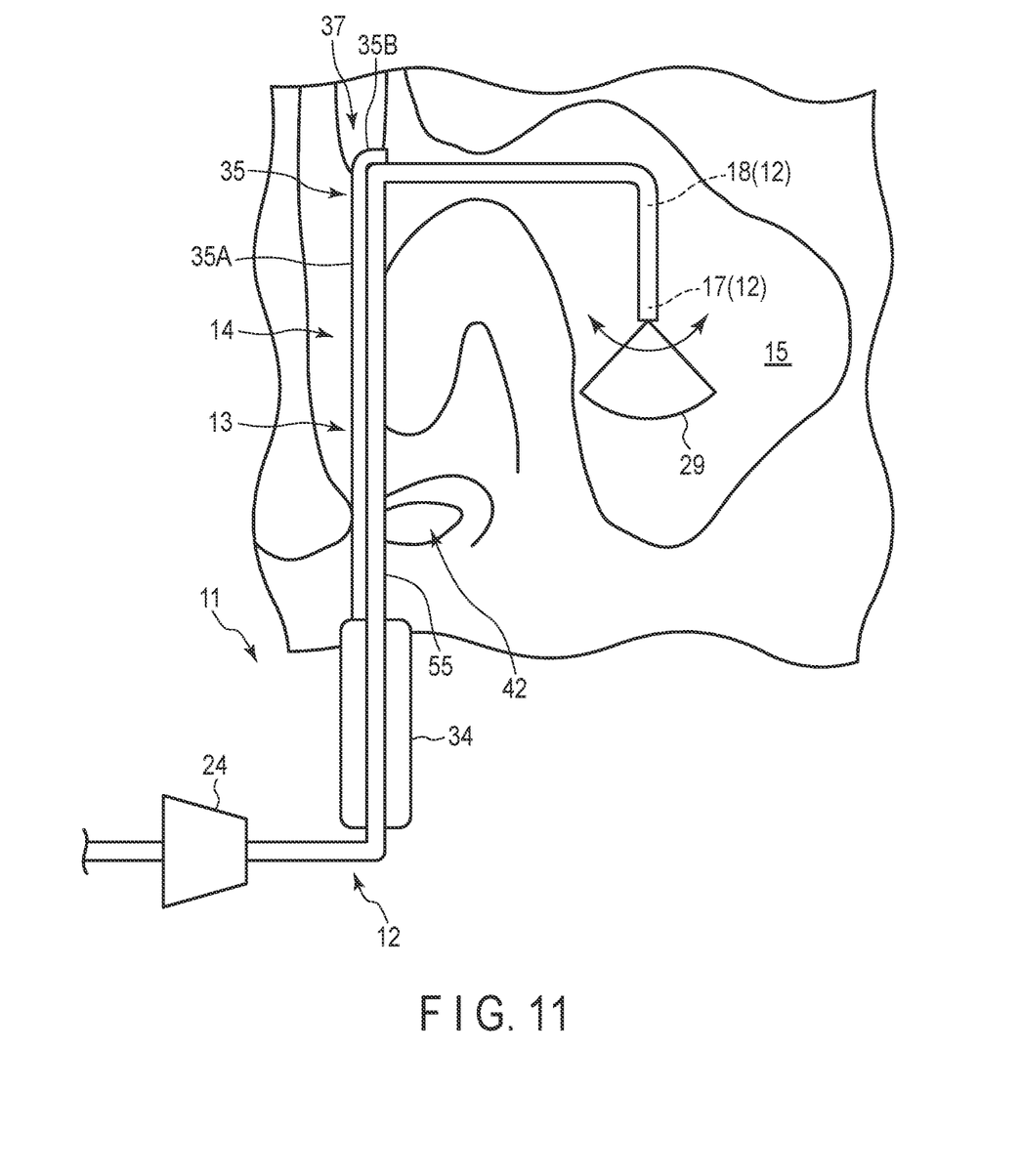
FIG. 11 is a schematic view showing a state in which the endoscope of the endoscope system shown in FIG. 1 protrudes from the insertion assist device, with the endoscope positioned in an interior portion of the paranasal sinuses (maxillary sinus).
Figure 12:
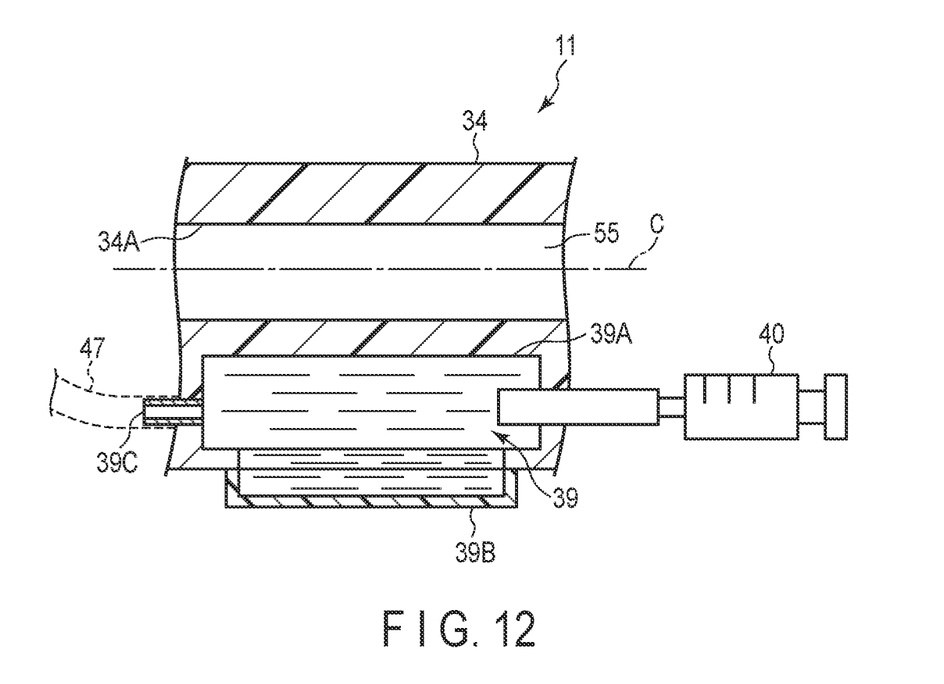
FIG. 12 is a cross-sectional view showing a step in which the liquid storage shown in FIG. 7 is filled with a liquid by a syringe.

In the present embodiment, the endoscope 12 has a structure capable of bending in the right-left direction (or the up-down direction). The bending direction of the bending portion 18 is an example; the bending portion 18 may be bent in the right-left direction as illustrated by the arrow in FIG. 11, may be bent to the back side and the front side as illustrated in FIG. 11, or may be bent in four directions (up, down, right, and left) by providing four wires 28.

As shown in FIG. 2, the illumination fiber 22 is optically connected to a light source provided adjacent to the controller 26. The illumination fiber 22 may emit illumination light to an exterior portion through the illumination lens 21. A plurality of light-receiving fibers 23 are optically connected to the image pickup device 25. A distal end of the light-receiving fiber 23 is exposed to an exterior portion by the light-receiving lens 31 in the vicinity of the distal component 17. This allows the endoscope 12 to acquire an image through the light-receiving fiber 23 at the distal component 17. The endoscope 12 can acquire an image around a central axis C shown in FIG. 2 through the light-receiving fiber 23.

As shown in FIG. 2, the endoscope 12 includes an image pickup device 25 configured of a CCD, a CMOS, etc. The endoscope 12 causes the image pickup device 25 to acquire an image. More specifically, the image pickup device 25 converts light from the light-receiving fiber 23 into an electrical signal and sends the electrical signal to the controller 26. The light-receiving fibers 23 receive return light from the subject and guide the light to the image pickup device 25. The image pickup device 25 sends the light received by light-receiving fibers 23 to the controller 26 as an electrical signal. The controller 26 converts the electrical signal into an image, appropriately processes the image, and displays the processed image on the display 27.

The controller 26 shown in FIG. 1 is configured by, for example, a general computer. The controller 26 is configured of a housing, a circuit substrate 32 built into the housing, a CPU, a ROM, and a RAM mounted on the circuit substrate 32, and a hard disk drive (HDD) 33 provided separately from the circuit substrate. The controller 26 can process an electrical signal corresponding to the image acquired by the image pickup device 25 of the insertion portion 16 for conversion into an image, and display the image (endoscopic image) on the display 27.

As shown in FIGS. 1, 3, 5 and 7, the insertion assist device 13 includes: a grip 34 which configures a portion gripped by a user's hand; a rail 35 linearly protruding from the grip 34; an operation lever 36 provided on the grip 34; a liquid storage 39 provided on an interior portion of the grip 34 and configured to store a liquid for treatment; and a sheath 55 provided on an exterior portion of the endoscope 12.

Figure 13:
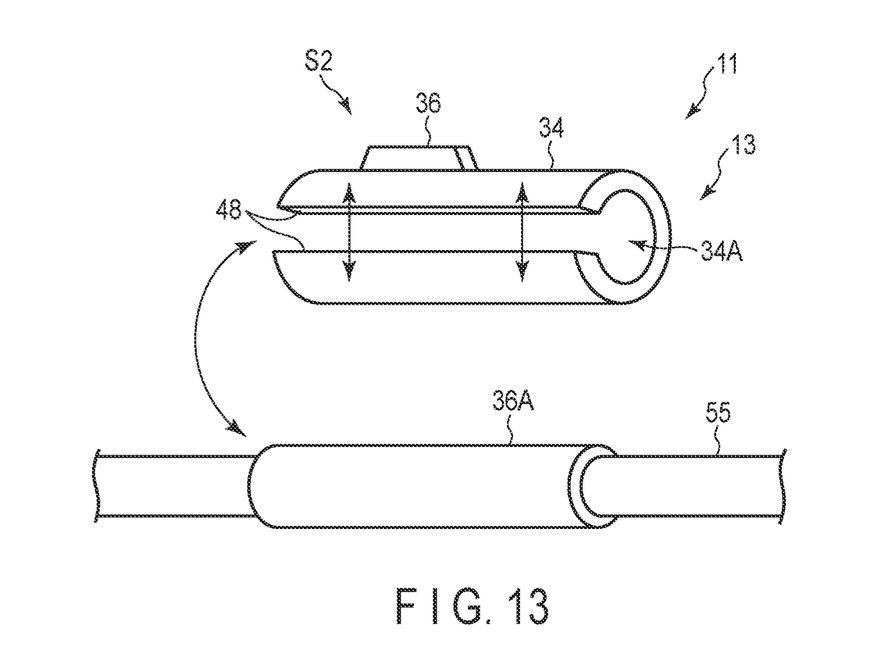
FIG. 13 is a perspective view showing a grip in a second state in which the grip can be attached to and detached from the sheath in the endoscope system shown in FIG. 1.
Figure 14:
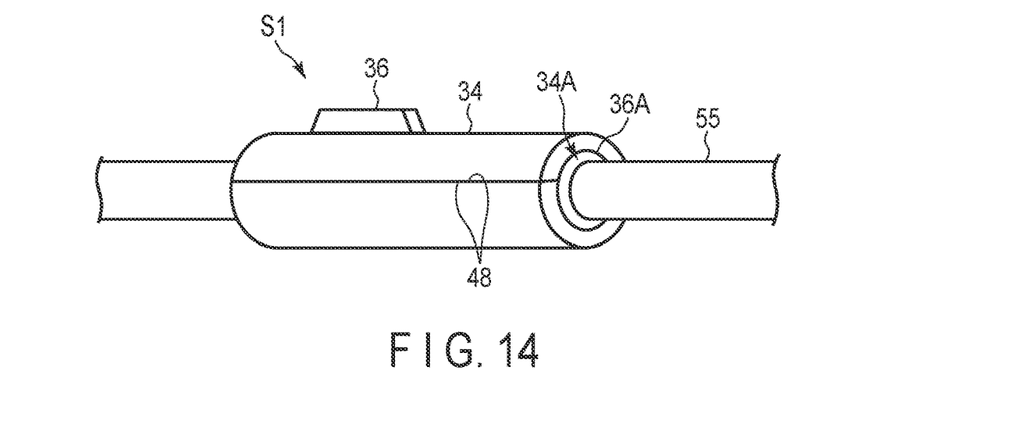
FIG. 14 is a perspective view showing a grip in a first state in which the grip is fixed to the sheath in the endoscope system of FIG. 1.

As shown in FIGS. 13 and 14, the grip 34 has a tubular (cylindrical) shape. The grip 34 includes a channel 34A through the inside of which the endoscope 12 is inserted, and paired open ends 48, 48 which communicate with the channel 34A. The grip 34 is formed of, for example, a resin material which has flexibility. The grip 34 is deformable between a first state S1 in which the paired open ends 48 and 48 are adjacent to, or abut against each other, and a second state S2 in which the paired open ends 48, 48 are separated from each other to allow the endoscope 12 to be inserted into and removed from the channel 34A. As shown in FIG. 14, the grip 34 in the first state S1 has a tubular shape that surrounds the periphery of the channel 34A. In the first state S1, the grip 34 is fixed to the sheath 55. In the second state S2, the grip 34 can be attached to and detached from the sheath 55 (endoscope 12) through the open ends 48, as shown in FIG. 13. In FIG. 13, a holding member 36B (to be described later) is attached in advance to the outer side of the sheath 55 (endoscope 12). The grip 34 includes a fixture for fixing the open ends 48, 48 to each other to maintain the first state S1. The fixture is configured by, for example, a screw, but is not limited thereto, and may be, for example, a fastener, an engagement structure with a claw, etc.

Figure 3:
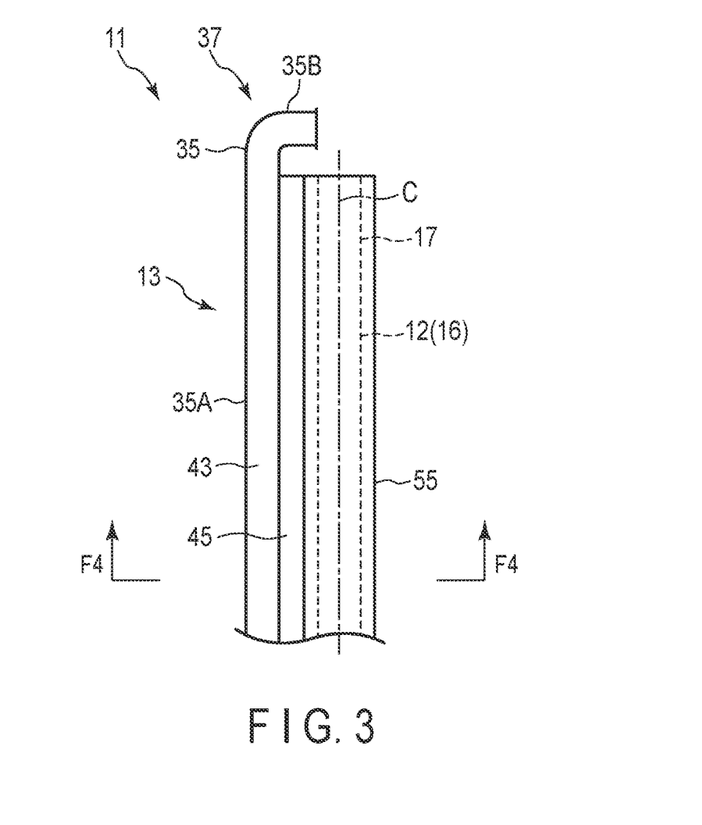
FIG. 3 is a schematic view showing an insertion assist device, an endoscope, a slider, and a sheath of the endoscope system shown in FIG. 1.

As shown in FIG. 1, the rail 35 is provided so as to be continuous with the grip 34, and is configured to guide the endoscope 12. As shown in FIG. 3, the rail 35 includes a linear portion 35A connected to the grip 34 at one end, an intersecting portion 35B provided continuously with the other end of the linear portion 35A, and a field-of-view widening portion 37 provided at at least one of the linear portion 35A and the intersecting portion 35B. The linear portion 35A extends linearly in, for example, the same direction as the direction in which the grip 34 extends.

It is preferable that the rail 35 be formed of, for example, a transparent resin material. Herein, the concept of "transparent" includes, for example, semi-transparent. It is preferable that the rail 35 be configured of a transparent material such as a polycarbonate resin or an acrylic resin. In the case of an acrylic resin, it is preferable, for example, that a polymethyl methacrylate resin (PMMA) be used. The field-of-view widening portion 37 is configured of the transparent rail 35, namely, the entirety of the linear portion 35A and the entirety of the intersecting portion 35B. In the present embodiment, the entire rail 35 is formed of a transparent resin material; however, the linear portion 35A (to be described later) need not be transparent, while it is preferable that at least the intersecting portion 35B (to be described later) be formed of a transparent resin material. In the present embodiment, the field-of-view widening portion 37 is configured of the entirety of the linear portion 35A and the entirety of the intersecting portion 35B. However, the configuration is not limited thereto, and only the intersecting portion 35B may be formed of a transparent resin material, with the field-of-view widening portion 37 configured of the entirety of the intersecting portion 35B.

Figure 4:
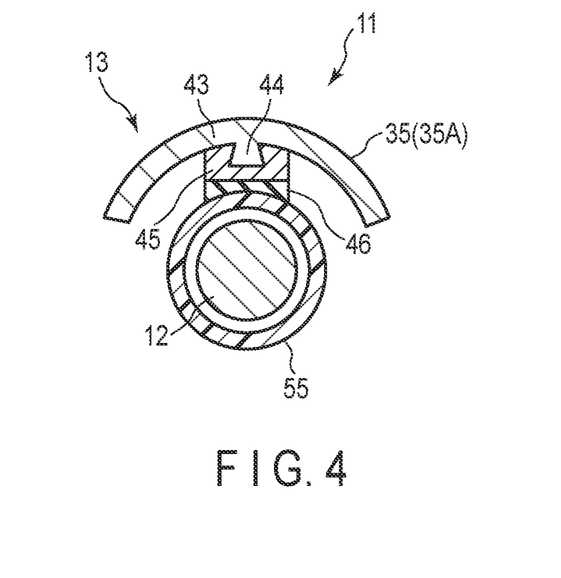
FIG. 4 is a cross-sectional view of the endoscope system shown in FIG. 3 taken at a position along line F4-F4.

A distal end portion of the rail 35 is laterally bent to form a substantially "L" shape as a whole. The rail 35 is a holding mechanism which holds the endoscope 12 (soft endoscope) in a predetermined shape along the linear portion 35A. As shown in FIG. 4, a cross-sectional shape of the rail 35 cut along a plane intersecting (orthogonal to) the central axis C of the endoscope 12 is either an arc-like or substantially tabular shape that follows the cross-sectional shape of the columnar endoscope 12.

As shown in FIGS. 3 and 4, the rail 35 includes: a main body section 43; a guide 44 that protrudes from the main body section 43 to form a continuous protrusion along the longitudinal direction of the rail 35 (linear portion 35A) (the direction of the central axis C of the endoscope 12); a slider 45 that can slidably move relative to the guide 44; and a fixing portion 46 that fixes the slider 45 and the sheath 55. The guide 44 is provided over the entire length of the rail 35 (the linear portion 35A and the intersecting portion 35B) in the longitudinal direction. The slider 45 can be fitted onto the outer side of the guide 44 and can slidably move along the guide 44. The slider 45 is formed of, for example, a flexible material, and can be bent along the bend of the rail 35. The fixing portion 46 is configured of, for example, a sheet having adhesiveness on both surfaces, that is, a so-called double-sided tape. Alternatively, the slider 45 and the sheath 55 may be integrally formed, with the fixing portion 46 omitted.

The sheath 55 is formed of a resin material (e.g., rubber) having flexibility in a tubular shape. The sheath 55 covers and protects the outer periphery of the endoscope 12. A liquid delivered from the liquid storage 39 is allowed to pass through an interior portion of the sheath 55. The sheath 55 is an example of a tubular member that is provided on an exterior portion of the endoscope 12. The sheath 55 is connected to the liquid storage 39 (via the connecting tube 47) at one end, and guides the liquid toward the other end opposite to the one end. In this case, the sheath 55 includes an opening provided at the other end of the sheath 55, that is open along the direction (longitudinal direction) in which the endoscope 12 advances and retreats. Similarly, the sheath 55 is an example of a tubular member that is provided on an exterior portion of the endoscope 12. The sheath 55 is connected to a suction device 62 (via the connecting tube 47) at one end, and is introduced into a sinus of the examinee at the other end opposite to the one end to remove by suction an undesired substance in the sinus.

Figure 5:
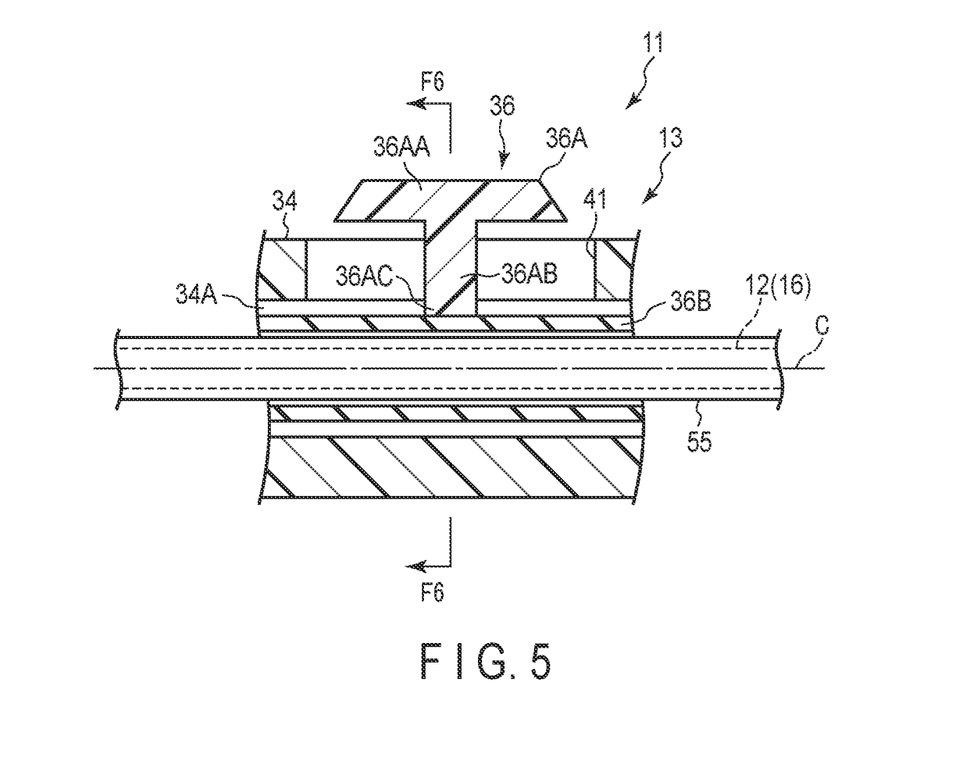
FIG. 5 is a cross-sectional view of the sheath, a grip, and a lever of the endoscope system shown in FIG. 1, cut along a plane passing through a central axis C of an insertion portion of the endoscope.
Figure 6:
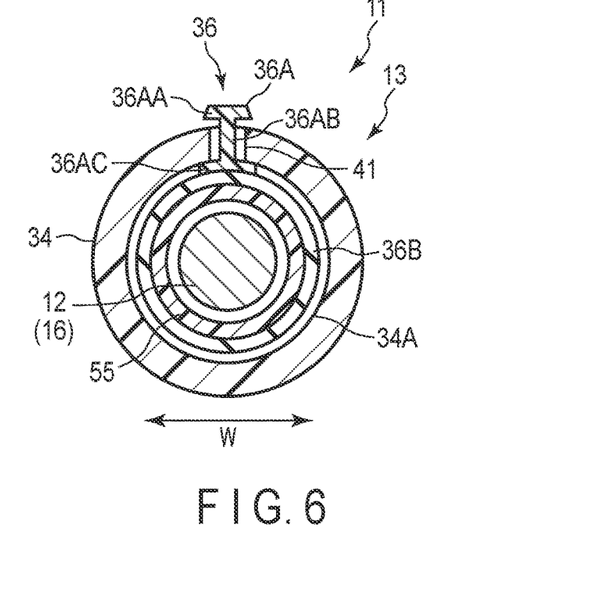
FIG. 6 is a cross-sectional view of the endoscope system shown in FIG. 5 taken at a position along line F6-F6.

As shown in FIGS. 5 and 6, the lever 36 includes a lever main body 36A and a holding member 36B against which a lever main body 36A abuts. The lever main body 36A is formed of a hard resinous material. The holding member 36B is configured in a tubular (cylindrical) shape using, for example, a resin material having a rubber-like elasticity. The holding member 36B is provided to surround part of an outer peripheral surface of the sheath 55. The lever main body 36A may be molded integrally with the holding member 36B (2-color molding). The grip 34 includes an elongated hole 41 through which a shaft portion of the lever main body 36A is passed. In the present embodiment, the lever main body 36A and the sheath 55 are fixed to each other by means of a frictional force using the holding member 36B, thus causing the sheath 55 (endoscope 12) to advance and retreat. However, the mode of fixation between the lever main body 36A and the sheath 55 is not limited thereto, and the lever main body 36A may be fixed to the sheath 55 by screwing, etc.

The lever main body 36A includes: a head portion 36AA; a shaft portion 36AB connected to the head portion 36AA at one end; and an anti-slip portion 36AC connected to the other end of the shaft portion 36AB. A width dimension of the head portion 36AA of the lever main body 36A is larger than a width dimension of the elongated hole 41, as viewed in a width direction W intersecting the direction of the central axis C. This prevents the head portion 36AA from entering the inside of the elongated hole 41, even when the user presses the head portion 36AA. Similarly, the width dimension of the anti-slip portion 36AC is larger than the width dimension of the elongated hole 41 as viewed in the width direction W, to prevent the lever main body 36A from slipping from the elongated hole 41.

Figure 8:
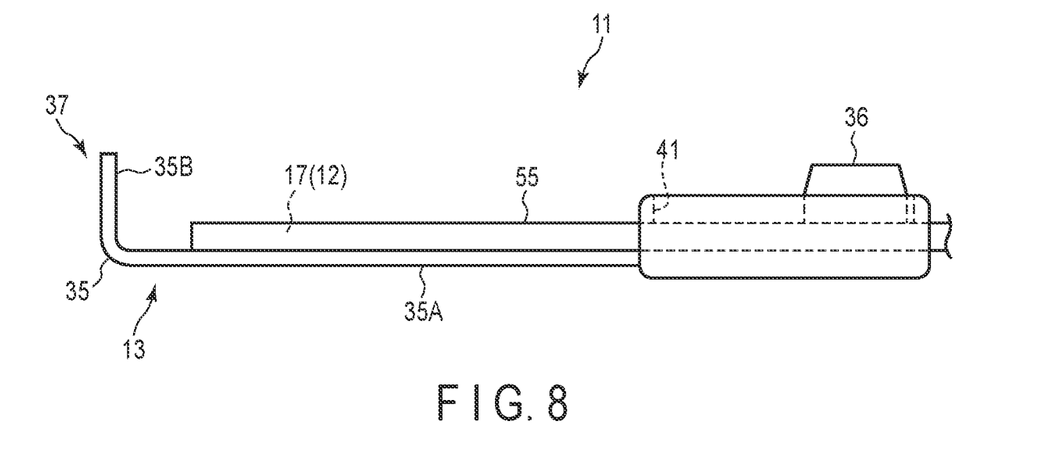
FIG. 8 is a schematic view schematically showing the insertion assist device, an endoscope at a position along a linear portion of the insertion assist device, and a lever of the endoscope system shown in FIG. 1.
Figure 9:
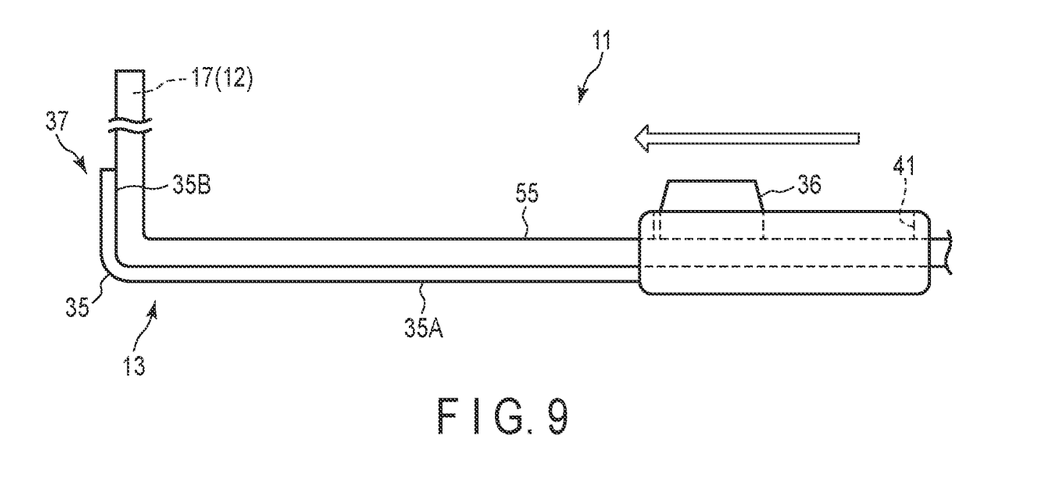
FIG. 9 is a schematic view schematically showing an insertion assist device, an endoscope at a position protruding from the insertion assist device, and a lever of the endoscope system shown in FIG. 1.

The lever 36 can slidably move along the elongated hole 41. The lever 36 is configured to be engageable with the sheath 55 by means of a frictional force of the holding member 36B. By causing the lever 36 to advance and retreat, as shown in FIGS. 8 and 9, the user can cause the endoscope 12 to protrude from the insertion assist device 13, or place the endoscope 12 back into the insertion assist device 13. The lever 36 is an example of an operation portion that abuts against an outer peripheral surface of the sheath 55 (tubular member) and causes the sheath 55 to advance and retreat together with the endoscope 12 by means of a frictional force with the outer peripheral surface.

Figure 7:
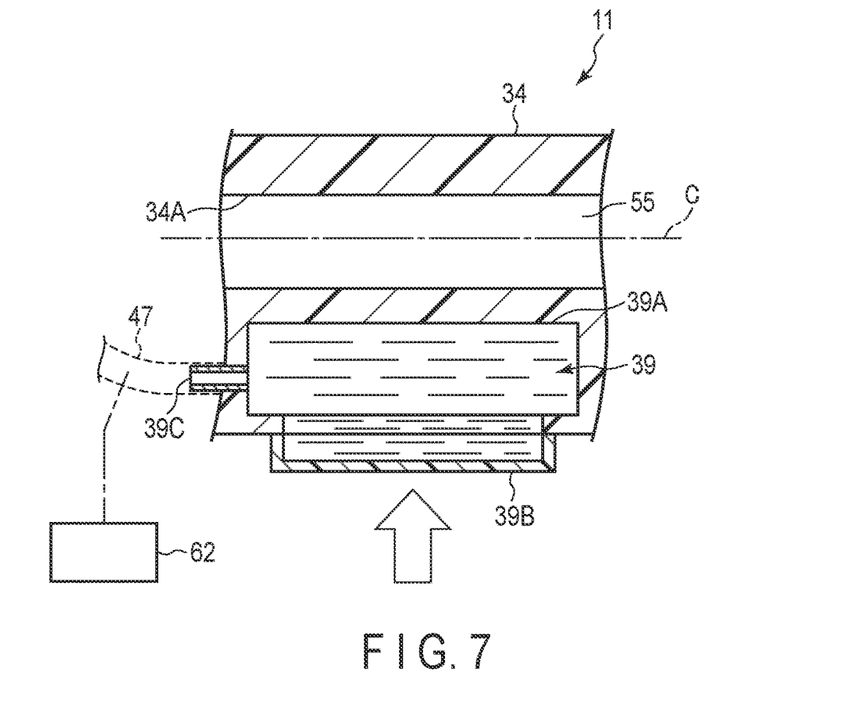
FIG. 7 is a cross-sectional view of a liquid storage of the insertion assist device of the endoscope system shown in FIG. 1, cut along a plane passing through the central axis C.

As shown in FIG. 7, the liquid storage 39 defines the periphery of a cavity formed in an interior portion of the grip 34. A liquid is stored in an interior portion (cavity portion) of the liquid storage 39. The liquid is configured of, for example, a drug solution for treating rhinitis or the like, but may be another liquid such as physiological saline. The liquid storage 39 includes a hard portion 39A formed of a hard resin material or the like, a protrusion 39B formed of a material (elastic member) having a rubber-like elasticity, a liquid extraction port 39C connected to the hard portion 39A, and a valve that seals the liquid extraction port 39C. The cavity in the liquid storage 39 can be filled with a liquid for treatment or other liquids such as physiological saline using a syringe 40 shown in FIG. 12.

When the protrusion 39B is not pressed, the valve seals the liquid extraction port 39C. When the protrusion 39B is depressed by the user's finger, the valve opens, causing the liquid to be delivered toward the sheath 55 via the liquid extraction port 39C. The liquid extraction port 39C and sheath 55 are connected by a connecting tube 47.

Next, an observation method (treatment method) of the nasal cavity 14 and the paranasal sinuses using the endoscope system 11 of the present embodiment will be described, with reference to FIGS. 1 and 8 to 11.

The user introduces the endoscope 12 into the inside of the sheath 55. The sheath 55 is fixed in advance to the slider 45 by the fixing portion 46. The slider 45 is introduced into the guide 44 of the rail 35 to integrate the rail 35 and the sheath 55. In this state, the user can introduce the endoscope 12 and the insertion assist device 13 into the nasal cavity 14 of the examinee.

As shown in FIG. 1, the user introduces a distal end of the insertion assist device 13 into a nasal cavity 14 of the examinee from an external nostril 42. At this time, a distal end portion of the insertion assist device 13 can be advanced toward the back of the nasal cavity 14, while allowing the endoscope 12 to have a down view of the interior of the nasal cavity 14. At this time, a distal end portion (intersecting portion 35B) of the insertion assist device 13 is shown, together with the nasal cavity 14, in a field of view 29 of the endoscope 12. At this time, a more favorable field of view 29 is ensured if the rail 35 is transparent, since the field of view 29 of the endoscope 12 will not be blocked by the rail 35. This prevents the user from accidentally hitting the distal end of the rail 35 of the insertion assist device 13 against the inner wall or the like of the nasal cavity 14.

In this state, the lever 36 is moved (advanced) in the direction of the arrow, as shown in FIGS. 8 and 9. At this time, when the user depresses the head portion 36AA of the lever 36 in the state shown in FIGS. 5 and 6, the anti-slip portion 36AC of the lever 36 deforms the holding member 36B, thereby increasing the contact area between the holding member 36B and the sheath 55. Thereby, a large frictional force is generated between the holding member 36B and the sheath 55, allowing the holding member 36B to grip the sheath 55. When the lever 36 is moved (advanced) in this state, the sheath 55 (endoscope 12) is moved (advanced) together with the lever 36. In this manner, the sheath 55 (endoscope 12) protrudes from the rail 35 of the insertion assist device 13.

Figure 10:
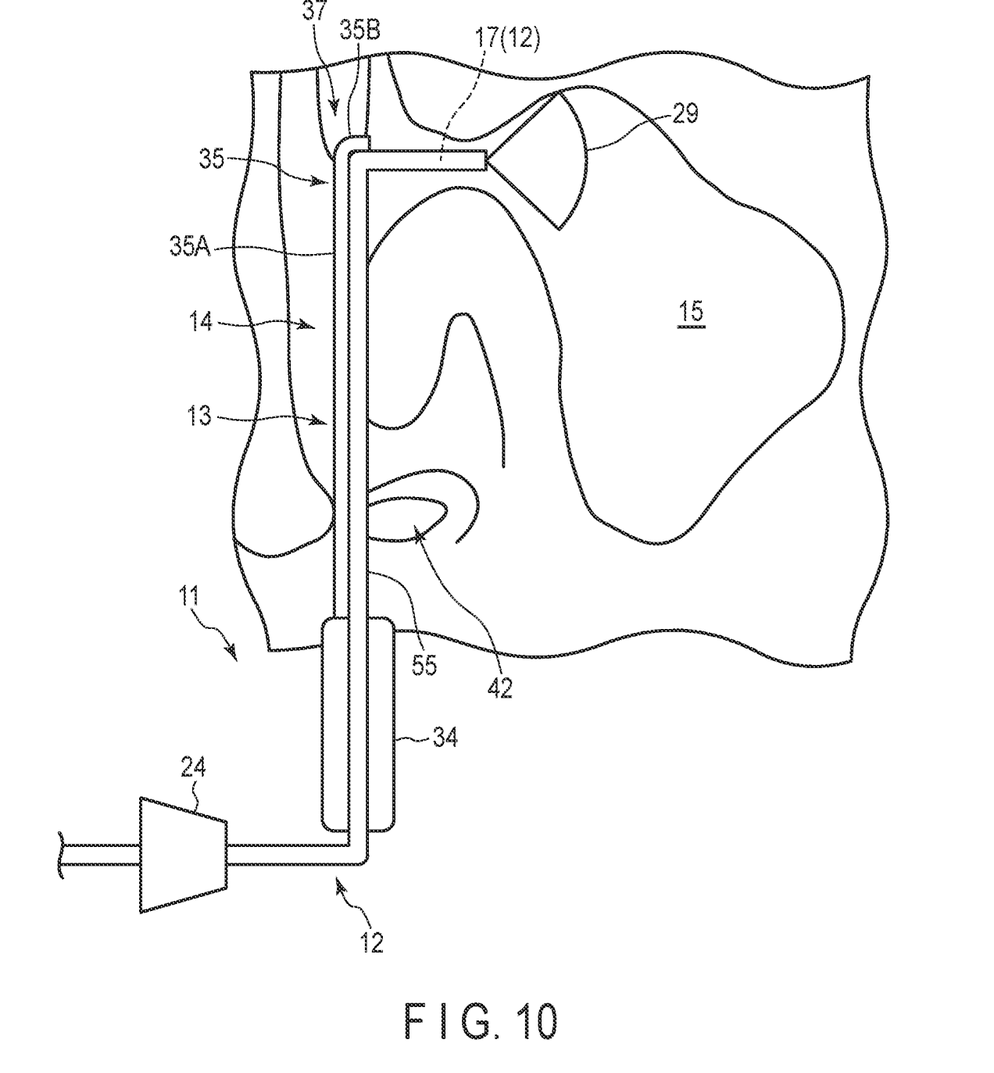
FIG. 10 is a schematic view showing a state in which the endoscope of the endoscope system shown in FIG. 1 protrudes from the insertion assist device, with the endoscope positioned in the vicinity of an entrance of the paranasal sinuses (maxillary sinus).

At this time, the distal component 17 of the endoscope 12 is moved in position from a state of extending along the linear portion 35A of the rail 35 to a state of extending along the intersecting portion 35B, and the direction in which the distal component 17 extends is changed by approximately 90°. Thereby, the state shown in FIG. 10 is obtained. At this time, the user can cause the endoscope 12 to advance into the maxillary sinus 15 by further moving the lever 36 in the direction of the arrow in FIG. 9, while capturing the entrance of the maxillary sinus 15 (paranasal sinuses) at the front based on the image obtained by the endoscope 12. As shown in FIG. 11, the user can observe the interior of the maxillary sinus 15 by operating the handle 24 to make the endoscope 12 bend using the bending portion 18, with the distal component 17 of the endoscope 12 reaching the interior of the maxillary sinus 15. Also, the user can perform a treatment on the interior of the maxillary sinus 15 as necessary. On this occasion, various treatments can be performed by using a treatment tool passed through an interior portion of the channel of the endoscope 12. Also, the user can also remove the endoscope 12 from the sheath 55, and then inject a liquid into the maxillary sinus 15 (paranasal sinuses) via the sheath 55. Thereby, the liquid can be applied to the inner wall inside the maxillary sinus 15. Alternatively, a branch portion may be provided at the connecting tube 47, and a proximal end portion of the sheath 55 may be connected to the suction device 62 such as a vacuum pump via the branch portion. The user can remove the endoscope 12 from the sheath 55, and then perform a treatment of removal by suction of pus (an desired substance) gathered in the maxillary sinus 15 (in the sinus of the examinee) by a distal end portion of the sheath 55. On this occasion, the endoscope 12 is prevented from being contaminated with the pus (undesired substance). In this case, it is preferable that a withdrawal portion (withdrawal bin) be interposed between the branch portion and the suction device 62, and an undesired substance is withdrawn into the withdrawal portion. After the application of the liquid, or after the suction and removal of the pus (undesired substance), the endoscope 12 can be introduced back into the interior portion of the sheath 55, as necessary.

After completion of the observation or treatment of the inside of the maxillary sinus 15, the user moves (retracts) the lever 36 in a direction opposite to the direction of the arrow in FIG. 9, thus placing the endoscope 12 into the insertion assist device 13. In this state, the insertion assist device 13 can be safely extracted from the nasal cavity 14 of the examinee, while allowing the endoscope 12 to have a down view of the nasal cavity 14 and the insertion assist device 13. When the endoscope 12 is removed prior to the liquid injection, the insertion assist device 13 is extracted from the inside of the nasal cavity 14, without using the endoscope 12. In the present embodiment, a liquid is injected into the paranasal sinuses of the examinee using the interior portion of the sheath 55 as a flow path; however, part of the flow path may be formed in an interior portion of the rail 35.

According to the present embodiment, the following can be said. The insertion assist device for an endoscope attached to the endoscope 12 includes: a grip 34 including a channel 34A through the inside of which the endoscope 12 is inserted; an operation portion engaged with the endoscope 12 and configured to move forward and backward relative to the grip 34 to cause the endoscope 12 to advance and retreat; a liquid storage 39 provided on an interior portion of the grip 34 and configured to store a liquid; and a tubular member provided on an interior portion or an exterior portion of the endoscope 12, connected to the liquid storage 39 at one end, and configured to guide the liquid toward the other end opposite to the one end.

The endoscope system 11 includes the insertion assist device 13 and the endoscope 12 to be inserted through the channel 34A of the insertion assist device 13.

With the above-described configuration, it is possible to observe the sinus of the examinee with the endoscope 12, and to inject a liquid into the sinus to be observed by using the tubular member as necessary. Thereby, when application of a liquid to a site to be observed is required as a result of the observation, the liquid can be injected into (applied to) the observation position using the tubular member. This eliminates the necessity to replace the equipment for liquid injection (application), thus improving the convenience of the user and allowing the liquid application treatment to be performed quickly.

The insertion assist device for an endoscope includes: a grip 34 attached to the endoscope 12 and including a channel 34A through the inside of which the endoscope 12 is inserted; an operation portion engaged with the endoscope 12 and configured to move the endoscope 12 forward and backward relative to the grip 34 to cause the endoscope 12 to advance and retreat; and a tubular member provided on an exterior portion of the endoscope 12 to cover the endoscope 12, connected to a suction device 62 at one end, and introduced into the sinus of the examinee at the other end opposite to the one end to remove by suction an undesired substance in the sinus.

With this configuration, it is possible to remove by suction an undesired substance in the sinus of the examinee using the tubular member provided on an exterior portion of the endoscope. This eliminates the necessity to replace the equipment for suction and removal, thus improving the convenience of the user.

The tubular member is provided on an exterior portion of the endoscope 12 so as to surround the periphery of the endoscope 12, and the endoscope 12 can be introduced into and extracted from the tubular member. With this configuration, it is possible to inject a liquid into the sinus of the examinee, using a tubular member that is externally provided to protect the endoscope 12. On this occasion, it is possible to prevent the endoscope 12 from being exposed to the liquid by removing the endoscope 12 from the tubular member. Thereby, it is possible to prevent advancement of deterioration of the endoscope 12 over time due to repeated exposure to the liquid. After completion of the injection of the liquid, the endoscope 12 can be placed back into the tubular member as necessary. Thereby, it is possible, for example, to confirm the state of completion of the liquid injection using the endoscope 12.

The operation portion abuts against an outer peripheral surface of the tubular member, and causes the tubular member to advance and retreat together with the endoscope 12 by means of a frictional force with the outer peripheral surface. With this configuration, it is possible to cause the endoscope 12 to advance and retreat with a simple structure using a frictional force. Thereby, the structure can be simplified, and the manufacturing cost of the insertion assist device 13 can be reduced.

A grip 34, which includes paired open ends 48, 48 that communicate with a channel 34A, is deformable between a first state S1 in which the paired open ends 48, 48 are adjacent to, or abut against each other, and a second state S2 in which the paired open ends 48, 48 are separated from each other to allow the endoscope 12 to be inserted into and removed from the channel 34A. With this configuration, the grip 34 can be configured with a structure that can be easily attached to and detached from the endoscope 12.

The liquid is a drug solution for treatment. With this configuration, it is possible to perform not only the observation of the interior of the sinus of the examinee, but also treatment of the diseased part as necessary. Thereby, it is possible to improve the convenience of the user, while eliminating the necessity to replace the base material for treatment, thus reducing the burden on the patient.

A modification of the endoscope system 11 will be described with reference to FIGS. 15 and 16. In the following, descriptions will be given mainly of configurations different from those of the above-described embodiment, and descriptions and illustrations of configurations common to those of the above-described embodiment will be omitted.

[First Modification]

A first modification of the endoscope system 11 will be described with reference to FIG. 15. In the first modification, a configuration of the insertion assist device 13 is different from that of the above-described embodiment; however, the other configurations are the same as those of the above-described embodiment.

The insertion assist device 13 includes: a grip 34 which configures a portion gripped by a user's hand; a rail 35 linearly protruding from the grip 34; an operation lever 36 provided on the grip 34; a liquid storage 39 provided on an interior portion of the grip 34 and configured to store a liquid for treatment; a sheath 55 provided on an exterior portion of the endoscope 12; and a second lever 36 provided on the grip 34 and configured to adjust a direction (position) in which the rail 35 extends.

Figure 15:
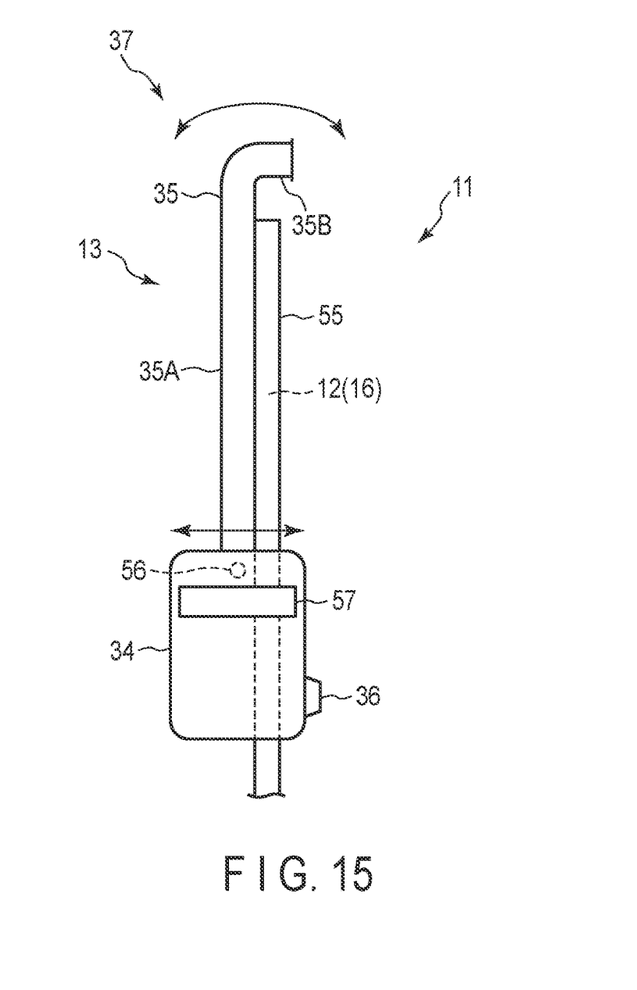
FIG. 15 is a schematic view showing an insertion assist device and an endoscope of an endoscope system according to a first modification.
Figure 16:
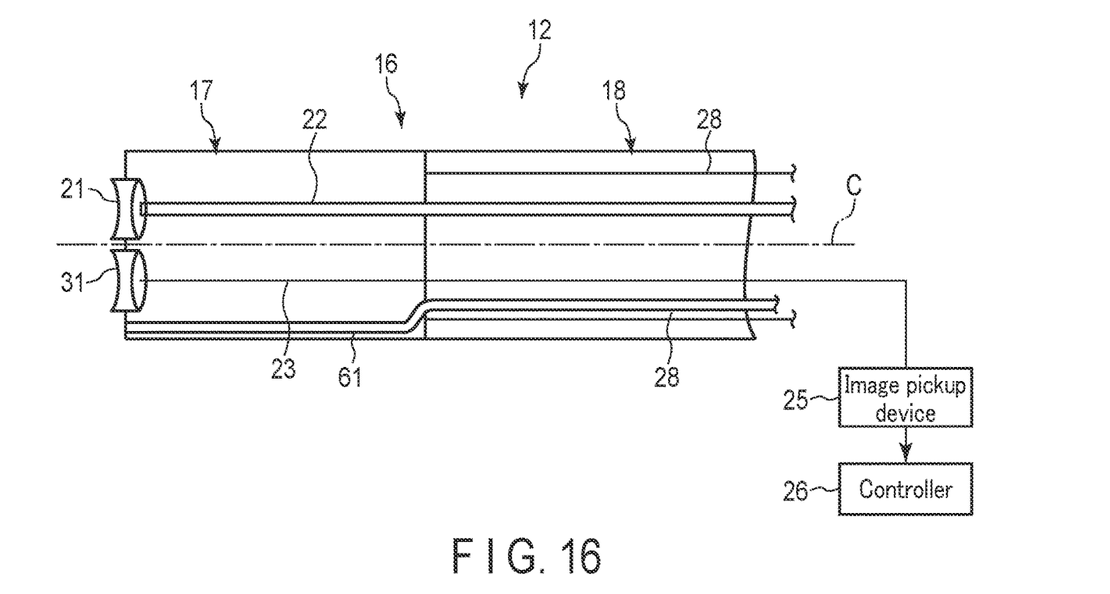
FIG. 16 is a schematic view showing the vicinity of a distal component of an endoscope of an endoscope system according to a second modification.

As shown in FIG. 15, the rail 35 includes: a linear portion 35A; a pin 56 provided at one end of the linear portion 35A; an intersecting portion 35B provided continuously with the other end of the linear portion 35A; and a field-of-view widening portion 37 provided at at least one of the linear portion 35A and the intersecting portion 35B. The linear portion 35A extends linearly in, for example, the same direction as the direction in which the grip 34 extends. The pin 56 is passed through a hole provided on the grip 34 (a boss protruding inside the grip 34), and is rotatably supported by the grip 34. This allows the rail 35, which is attached to the grip 34, to be pivoted about the pin 56 by a predetermined angle. One end of the linear portion 35A is connected to a second lever 57 at a further distal position than the pin 56. By operating the second lever 57, the user can finely adjust the direction in which the rail 35 extends.

The second lever 57 is an example of a second operation portion provided on the grip 34, and is configured to change the position of the rail 35.

It is preferable that the rail 35 be formed of, for example, a transparent resin material. In the present embodiment, the entire rail 35 is formed of a transparent resin material; however, the linear portion 35A (to be described later) need not be transparent, while it is preferable that at least the intersecting portion 35B (to be described later) be formed of a transparent resin material.

Next, an observation method of a nasal cavity 14 and the paranasal sinuses using the endoscope system 11 of the present embodiment will be described, with reference to FIG. 15, etc.

The user introduces the endoscope 12 into the inside of the sheath 55, to integrate the endoscope 12, the rail 35, and the sheath 55 in advance. In this state, the user can introduce the endoscope 12 and the insertion assist device 13 into the nasal cavity 14 of the examinee.

As shown in FIG. 1, the user introduces a distal end of the insertion assist device 13 into a nasal cavity 14 of the examinee from an external nostril 42. At this time, a distal end portion of the insertion assist device 13 can be advanced toward the back of the nasal cavity 14, while allowing the endoscope 12 to have a down view of the interior of the nasal cavity 14. At this time, a distal end portion (intersecting portion 35B) of the insertion assist device 13 is shown, together with the nasal cavity 14, in a field of view 29 of the endoscope 12. At this time, a more favorable field of view 29 is ensured if the rail 35 is transparent, since the field of view 29 of the endoscope 12 will not be blocked by the rail 35.

In this state, the lever 36 is moved (advanced) in the direction of the arrow, as shown in FIGS. 8 and 9. Thereby, the state shown in FIG. 10 is obtained. At this time, the user can cause the endoscope 12 to advance into the maxillary sinus 15 by further moving the lever 36 in the direction of the arrow in FIG. 9, while capturing the entrance of the maxillary sinus 15 (paranasal sinuses) at the front based on the image obtained by the endoscope 12. At this time, the user can finely adjust the position of the rail 35 (the direction in which the rail 35 extends) by operating the second lever 57. Thereby, various fine adjustments can be performed, for example, to make the endoscope 12 and the sheath 55 face each other with respect to the entrance of the maxillary sinus 15 (paranasal sinuses), or to avoid an obstacle present at the entrance of the maxillary sinus 15.

As shown in FIG. 11, the user can observe the interior of the maxillary sinus 15 by operating the handle 24 to make the endoscope 12 bend using the bending portion 18, with the distal component 17 of the endoscope 12 reaching the interior of the maxillary sinus 15. On this occasion, the user can also finely adjust the angle of the field of view 29 of the endoscope 12, by operating the second lever 57. Furthermore, the user can perform a treatment on the interior of the maxillary sinus 15 as necessary. On this occasion, various treatments can be performed by using a treatment tool passed through an interior portion of the channel of the endoscope 12. Also, the user can also remove the endoscope 12 from the sheath 55, and then inject a liquid into the maxillary sinus 15 (paranasal sinuses) by means of the sheath 55. Alternatively, by connecting the sheath 55 to a suction device such as a vacuum pump, it is possible to perform a treatment of removal by suction of pus gathered inside the maxillary sinus 15 by means of the sheath 55.

After completion of the observation or treatment of the inside of the maxillary sinus 15, the user moves (retracts) the lever 36 in a direction opposite to the direction of the arrow in FIG. 9, thus placing the endoscope 12 into the insertion assist device 13. In this state, the insertion assist device 13 can be safely extracted from the nasal cavity 14 of the examinee, while allowing the endoscope 12 to have a down view of the nasal cavity 14 and the insertion assist device 13.

According to the first modification, the insertion assist device 13 includes: a rail 35 provided so as to be continuous with the grip 34 and configured to guide the endoscope 12; and a second operation portion provided on the grip 34 and configured to change the position of the rail 35.

With this configuration, it is possible to change the position of the rail 35 using the second operation portion, and to finely adjust the position of the rail 35 while the insertion assist device 13 is being introduced into the sinus of the examinee. In addition, the angle of the field of view 29 of the endoscope 12 can be finely adjusted during observation of the interior of the sinus of the examinee. This improves the convenience of the user.

[Second Modification]

A second modification of the endoscope system 11 will be described with reference to FIG. 16. In the second modification, a sheath 55 is not provided on the periphery of the endoscope 12, unlike the above-described embodiment; however, the other configurations are the same as those of the above-described embodiment.

The insertion assist device 13 has the same configuration as that of the above-described embodiment except that the sheath 55 is not provided.

The endoscope 12 includes: an insertion portion 16 used for insertion into a nasal cavity 14, the paranasal sinuses (a maxillary sinus 15), etc.; a distal component 17 provided on the vicinity of a distal end of the insertion portion 16; a bending portion 18 provided on the proximal side with respect to the distal component 17 and configured to adjust a direction in which the distal component 17 extends; a channel through which a treatment tool that performs a predetermined treatment on the interior of the sinus is passed; an illumination lens 21; a plurality of illumination fibers 22; a plurality of light-receiving fibers 23; a handle 24 for applying various operations (e.g., a bending operation) to the insertion portion 16; a controller 26 electrically connected to the insertion portion 16 and the image pickup device 25 by power lines and various signal lines; and a display 27 connected to the controller 26.

The holding member 36B included in the lever 36 of the insertion assist device 13 is configured in a tubular (cylindrical) shape using, for example, a resin material having a rubber-like elasticity. The holding member 36B is provided to surround part of an outer peripheral surface of the endoscope 12. In this modification, the lever main body 36A and the endoscope 12 are fixed to each other by means of a frictional force using the holding member 36B, thus causing the endoscope 12 to advance and retreat.

The insertion assist device 13 includes a liquid delivery tube 61 passed through an interior portion of the insertion portion 16. The liquid delivery tube 61 is configured of a general flexible tube formed of a resin or the like. The liquid delivery tube 61 is provided on an interior portion of the endoscope 12. The liquid delivery tube 61 is connected to a liquid storage 39 at one end. The liquid delivery tube 61 can direct the liquid toward the other end (i.e., a distal end of the endoscope) opposite to the one end.

Next, an observation method (treatment method) of the nasal cavity 14 and the paranasal sinuses using the endoscope system 11 of the present embodiment will be described, with reference to FIGS. 1, 8 to 11, and 16.

The endoscope 12 is fixed in advance to a slider 45 with a fixing portion 46 (double-sided tape). Furthermore, the user introduces the slider 45 into the guide 44 of the rail 35 to integrate the rail 35 and the endoscope 12. In this state, the user can introduce the endoscope 12 and the insertion assist device 13 into the nasal cavity 14 of the examinee.

As shown in FIG. 1, the user introduces a distal end of the insertion assist device 13 into a nasal cavity 14 of the examinee from an external nostril 42. At this time, a distal end portion of the insertion assist device 13 can be advanced toward the back of the nasal cavity 14, while allowing the endoscope 12 to have a down view of the interior of the nasal cavity 14. At this time, a more favorable field of view 29 is ensured if the rail 35 is transparent, since the field of view 29 of the endoscope 12 will not be blocked by the rail 35.

In this state, the lever 36 is moved (advanced) in the direction of the arrow, as shown in FIGS. 8 and 9. At this time, when the user depresses the head portion 36AA of the lever 36, the anti-slip portion 36AC of the lever 36 deforms the holding member 36B, thereby increasing the contact area between the holding member 36B and the endoscope 12. Thereby, a large frictional force is generated between the holding member 36B and the endoscope 12, allowing the holding member 36B to grip the endoscope 12. When the lever 36 is moved (advanced) in this state, the endoscope 12 is moved (advanced) together with the lever 36. In this manner, the endoscope 12 protrudes from the rail 35 of the insertion assist device 13. Thereby, the state shown in FIG. 10 is obtained.

At this time, the user can cause the endoscope 12 to advance into the maxillary sinus 15 by further moving the lever 36 in the direction of the arrow in FIG. 9, while capturing the entrance of the maxillary sinus 15 (paranasal sinuses) at the front based on the image obtained by the endoscope 12. As shown in FIG. 11, the user can observe the interior of the maxillary sinus 15 by operating the handle 24 to make the endoscope 12 bend using the bending portion 18, with the distal component 17 of the endoscope 12 reaching the interior of the maxillary sinus 15. Also, the user can perform a treatment on the interior of the maxillary sinus 15 as necessary. On this occasion, various treatments can be performed by using a treatment tool passed through an interior portion of the channel of the endoscope 12.

In this modification, since the liquid delivery tube 61 is provided on the endoscope 12, removal of the endoscope 12 is not required before the liquid is injected (applied) into the maxillary sinus 15. The user can inject a liquid into the maxillary sinus 15 (paranasal sinuses) or apply a liquid onto the inner wall of the maxillary sinus 15 using the liquid delivery tube 61 built into the endoscope 12.

After completion of the observation or treatment of the inside of the maxillary sinus 15, the user moves (retracts) the lever 36 in a direction opposite to the direction of the arrow in FIG. 9, thus placing the endoscope 12 into the insertion assist device 13. In this state, the insertion assist device 13 can be safely extracted from the nasal cavity 14 of the examinee, while allowing the endoscope 12 to have a down view of the nasal cavity 14 and the insertion assist device 13.

According to the present modification, the tubular member is a liquid delivery tube 61 provided on an interior portion of the endoscope 12. With this configuration, removal of the endoscope 12 is not required when a liquid is injected into the sinus of the examinee, thus further improving the convenience of the user.

As a matter of course, a single endoscope system 11 can be achieved by suitably combining the constituent elements disclosed in the embodiment and its modifications.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion assist device comprising:
    a grip comprising a channel, the channel being configured to receive an insertion portion of an endoscope;
    a lever configured to advance the insertion portion by moving distally relative to the grip, and the lever being configured to retreat the insertion portion by moving proximally relative to the grip;
    a liquid container having a closed end, the container being provided on an interior of the grip and configured to store a liquid; and
    a tubular sheath provided on an exterior of the insertion portion of the endoscope, the tubular sheath being connected to the liquid container at a first end of the tubular sheath, and configured to guide the liquid toward a second end of the tubular sheath, the second end being opposite to the first end;
    wherein the grip includes a pair of open ends each formed along a longitudinal axis of the channel, and the pair of open ends are deformable between a closed state in which the pair of open ends are configured to prevent the endoscope from being inserted into or removed from the channel and an open state in which the pair of open ends are separated from each other to allow the endoscope to be inserted into or removed from the channel.

2. The insertion assist device according to claim 1, wherein the second end of the tubular sheath includes an opening extending in a direction in which the insertion portion of the endoscope advances and retreats.

3. The insertion assist device according to claim 1, wherein the tubular sheath is provided on the exterior of the insertion portion of the endoscope, and surrounds an outer peripheral surface of the insertion portion of the endoscope.

4. The insertion assist device according to claim 3, wherein the lever abuts against an outer peripheral surface of the tubular sheath, and advances or retreats together with the insertion portion of the endoscope by generating a frictional force between the outer peripheral surface of the tubular sheath and the lever.

5. The insertion assist device according to claim 1, wherein the pair of open ends abut against each other in the closed state.

6. The insertion assist device according to claim 1, further comprising a rail provided at a distal side of the grip, the rail being connected to the grip and configured to guide the insertion portion of the endoscope.

7. The insertion assist device according to claim 6, further comprising a second lever provided on the grip and configured to change a position of the rail.

8. The insertion assist device according to claim 7, wherein:
    the second lever includes a pin supported so as to be rotatable relative to a hole provided on the grip, and
    the rail is configured to pivot around an axis of the pin.

9. The insertion assist device according to claim 1, wherein the liquid is a drug solution for treatment.

10. The insertion assist device according to claim 1, wherein at least a portion of the liquid container is formed of an elastic member.

11. The insertion assist device according to claim 10, wherein:
    the liquid container includes a protrusion protruding from a surface of the grip, and
    the protrusion is formed of the elastic member.

12. The insertion assist device according to claim 10, wherein:
    the liquid container includes a hard portion formed of a material harder than the elastic member, and
    the hard portion is disposed in the interior of the grip.

13. The insertion assist device according to claim 12, further comprising:
    an extraction port connected to the hard portion and configured to connect the tubular sheath and the liquid container; and
    a valve provided at the extraction port and configured to seal the extraction port.

14. An endoscope system comprising:
    the insertion assist device according to claim 1; and
    the endoscope including the insertion portion inserted through the channel of the insertion assist device.

15. The endoscope system according to claim 14, further comprising a suction device, wherein the tubular sheath is provided on the exterior of the insertion portion of the endoscope, the tubular sheath surrounding an outer periphery of the endoscope and is connected to the suction device.

16. The endoscope system according to claim 1, wherein the liquid container being fixed in the grip relative to an entire range of motion of the lever.

17. An insertion assist device comprising:
    a grip comprising a channel, the channel being configured to receive an insertion portion of an endoscope;
    a lever configured to advance the insertion portion by moving distally relative to the grip, and the lever being configured to retreat the insertion portion by moving proximally relative to the grip;
    a liquid container, the container being enclosed within an interior of the grip and configured to store a liquid; and
    a tubular sheath provided on an exterior of the insertion portion of the endoscope, the tubular sheath being connected to the liquid container at a first end of the tubular sheath, and configured to guide the liquid toward a second end of the tubular sheath, the second end being opposite to the first end,
    wherein the liquid container being fixed in the grip relative to an entire range of motion of the lever,
    wherein the grip includes a pair of open ends each formed along a longitudinal axis of the channel, and the pair of open ends are deformable between a closed state in which the pair of open ends are configured to prevent the endoscope from being inserted into or removed from the channel and an open state in which the pair of open ends are separated from each other to allow the endoscope to be inserted into or removed from the channel.

18. The insertion assist device according to claim 17, wherein at least a portion of the liquid container is formed of an elastic member,
    wherein the liquid container includes a hard portion formed of a material harder than the elastic member, and
    the hard portion is disposed in the interior of the grip.

19. The insertion assist device according to claim 17, wherein at least a portion of the liquid container is formed of an elastic member, wherein the liquid container includes a protrusion protruding from a surface of the grip, and the protrusion is formed of the elastic member.

* * * * *